United States Patent [19]
Scott

[11] Patent Number: 5,474,568
[45] Date of Patent: Dec. 12, 1995

[54] INSTRUMENT FOR CLOSING TROCAR PUNCTURE WOUNDS

[75] Inventor: Ian M. Scott, Ridgefield, Conn.

[73] Assignee: United States Surgical Corporation, Norwalk, Conn.

[21] Appl. No.: 158,072

[22] Filed: Nov. 24, 1993

Related U.S. Application Data

[63] Continuation-in-part of Ser. No. 134,144, Oct. 8, 1993.

[51] Int. Cl.$^6$ ..................................................... A61B 17/00
[52] U.S. Cl. ........................ 606/144; 606/139; 606/148; 112/269
[58] Field of Search ..................................... 606/139, 144, 606/145, 147, 148, 151, 205, 207; 112/80.03, 169

[56] References Cited

U.S. PATENT DOCUMENTS

| | | |
|---|---|---|
| 1,037,864 | 9/1912 | Carlson et al. . |
| 1,449,087 | 3/1923 | Bugbee . |
| 1,822,330 | 9/1931 | Ainslie . |
| 2,108,206 | 2/1938 | Meeker . |
| 2,113,246 | 4/1938 | Wappler . |
| 2,213,830 | 9/1940 | Anastasi . |
| 2,579,192 | 12/1951 | Kohl . |
| 2,601,564 | 6/1952 | Smith . |
| 2,737,954 | 3/1956 | Knapp . |
| 2,790,437 | 4/1957 | Moore . |
| 2,959,172 | 11/1960 | Held . |
| 3,090,386 | 5/1963 | Curtis . |
| 3,168,097 | 2/1965 | Dormia . |
| 3,470,875 | 10/1969 | Johnson . |
| 3,807,407 | 4/1974 | Schweizer . |
| 3,871,379 | 3/1975 | Clarke . |
| 3,901,244 | 8/1975 | Schweizer . |
| 4,014,343 | 3/1977 | Esty . |
| 4,084,594 | 4/1978 | Mosior . |
| 4,345,601 | 8/1982 | Fukuda . |
| 4,493,323 | 1/1985 | Albright et al. . |
| 4,510,934 | 4/1985 | Batra . |
| 4,557,265 | 12/1985 | Andersson . |
| 4,569,131 | 2/1986 | Falk et al. . |
| 4,597,390 | 7/1986 | Mulhollan et al. . |
| 4,621,640 | 11/1986 | Mulhollan et al. . |
| 4,760,848 | 8/1988 | Hasson . |
| 4,890,615 | 1/1990 | Caspari et al. . |
| 4,923,461 | 5/1990 | Caspari et al. . |
| 4,924,851 | 5/1990 | Ognier et al. . |
| 4,935,027 | 6/1990 | Yoon . |
| 4,957,498 | 9/1990 | Caspari et al. . |
| 4,986,825 | 1/1991 | Bays et al. . |
| 5,129,912 | 7/1992 | Noda et al. . |
| 5,152,769 | 10/1992 | Baber . |
| 5,222,508 | 6/1993 | Contarini . |

(List continued on next page.)

FOREIGN PATENT DOCUMENTS

| | | |
|---|---|---|
| 0140557 | 5/1985 | European Pat. Off. . |
| 0478949 | 4/1992 | European Pat. Off. . |
| 0567130 | 10/1993 | European Pat. Off. . |
| 4137218 | 2/1993 | Germany . |
| 1093329 | 5/1984 | U.S.S.R. . |

OTHER PUBLICATIONS

REMA Brochure, REMA–Medizintechnik GmbH (believed to be published in 1992).
Valleylab Laparoscopic Instrumentation Brochure, 1991.
Cabot Medical Brochure, Corson Disposable Suction/Irrigation Probe, 1990.

*Primary Examiner*—Stephen C. Pellegrino
*Assistant Examiner*—Jeffrey A. Schmidt

[57] ABSTRACT

A surgical instrument for applying sutures through body tissue including a handle assembly, an elongated housing removably mounted to said handle assembly and having a proximal end portion and a distal end portion, at least one needle carrier operatively mounted in the distal end portion and movable between a retracted position and a deployed position, and a needle releasably retained in the needle carrier member. The instrument may also include a retaining mechanism adapted to retain the at least one needle carrier in the partially deployed position.

21 Claims, 20 Drawing Sheets

U.S. PATENT DOCUMENTS

| | | | |
|---|---|---|---|
| 5,250,056 | 10/1993 | Hasson | 606/208 |
| 5,281,235 | 1/1994 | Haber et al. | 606/148 |
| 5,281,237 | 1/1994 | Gimpelson | 606/139 |
| 5,282,817 | 2/1994 | Hoogeboom et al. | 606/208 |
| 5,308,358 | 5/1994 | Bond et al. . | |
| 5,320,632 | 6/1994 | Heidmueller . | |
| 5,334,199 | 8/1994 | Yoon | 606/144 |
| 5,364,408 | 11/1994 | Gordon . | |
| 5,368,601 | 11/1994 | Sauer et al. . | |

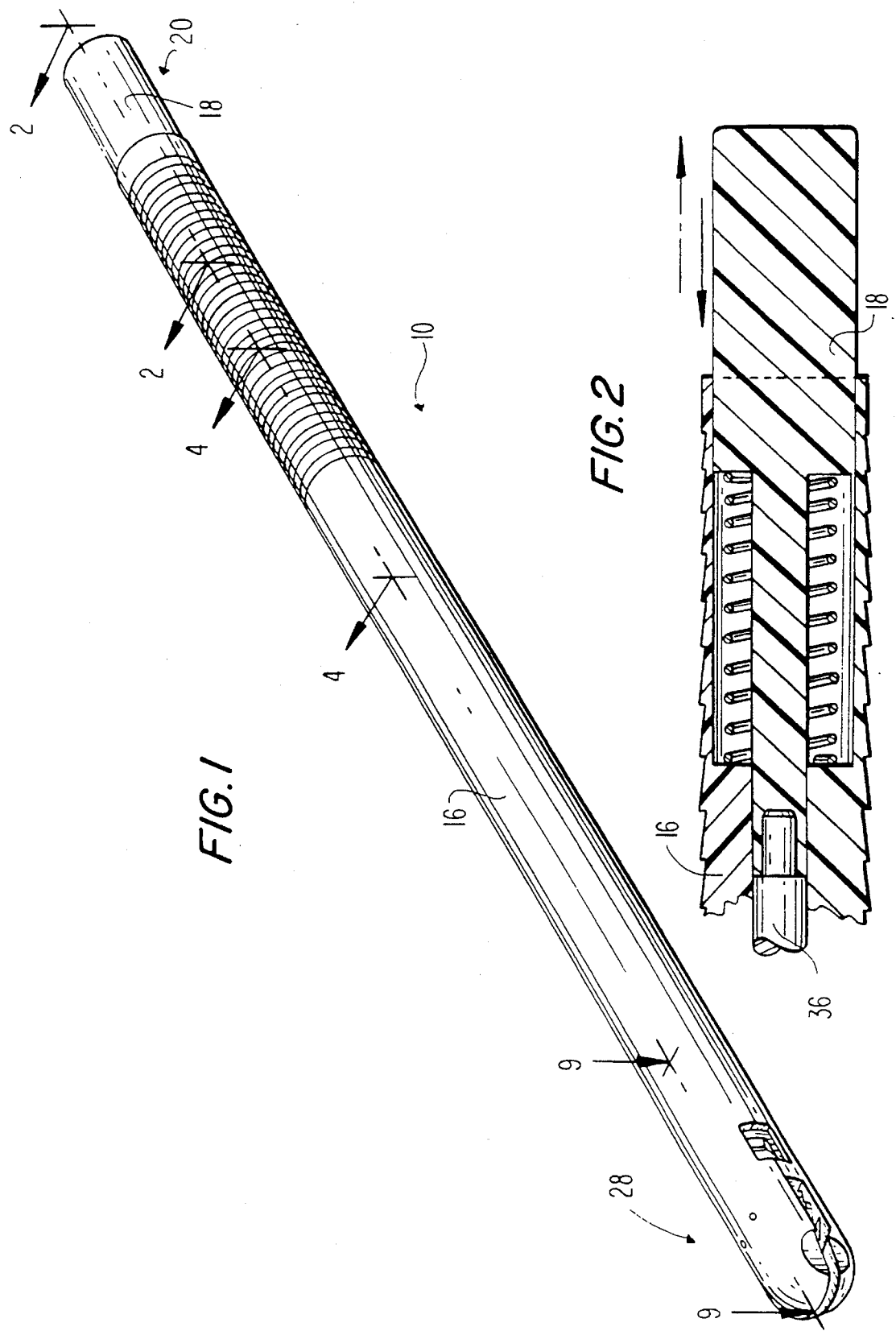

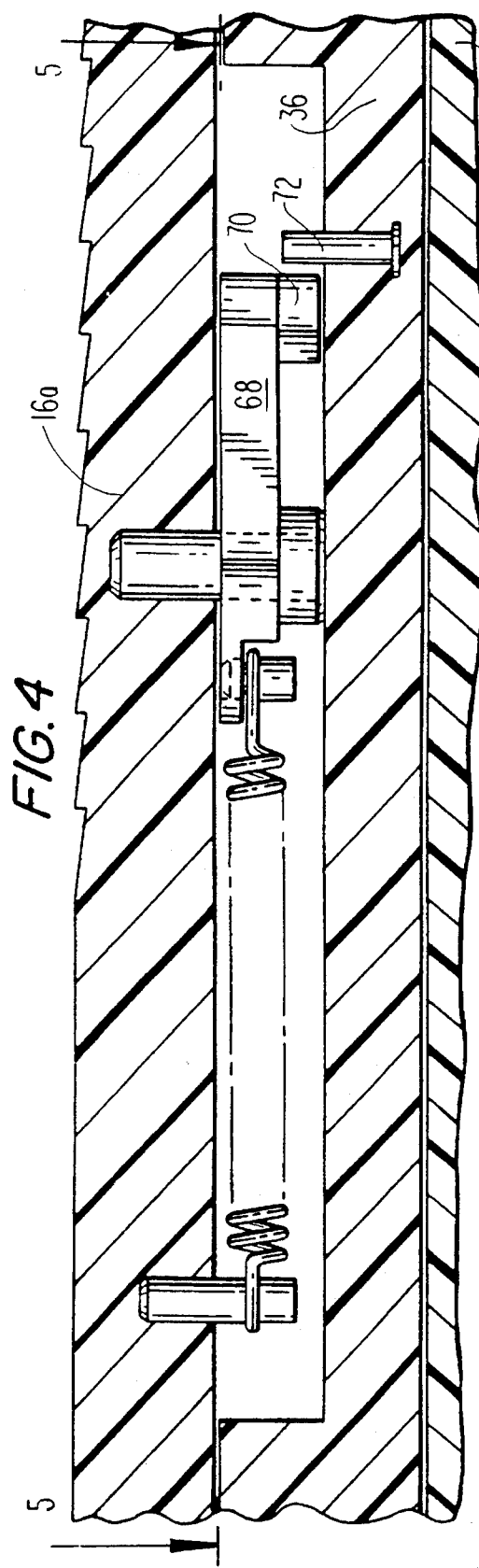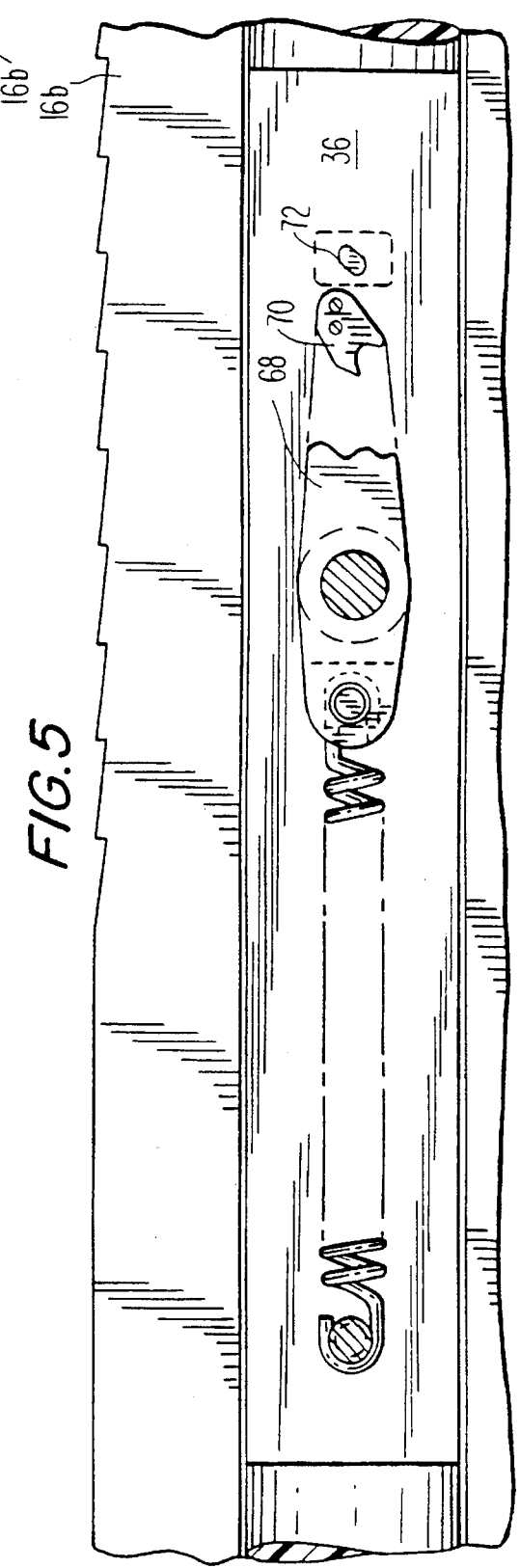

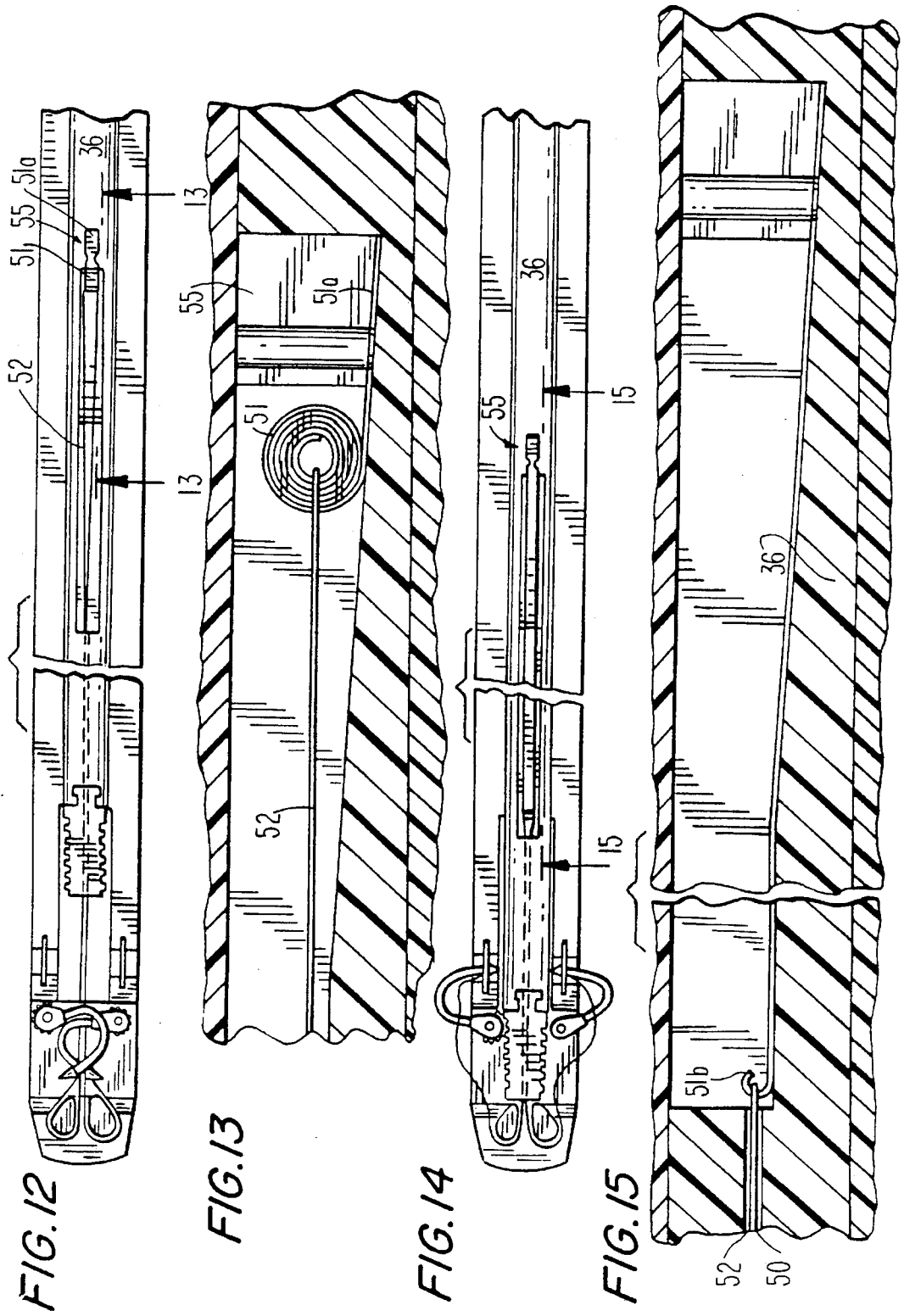

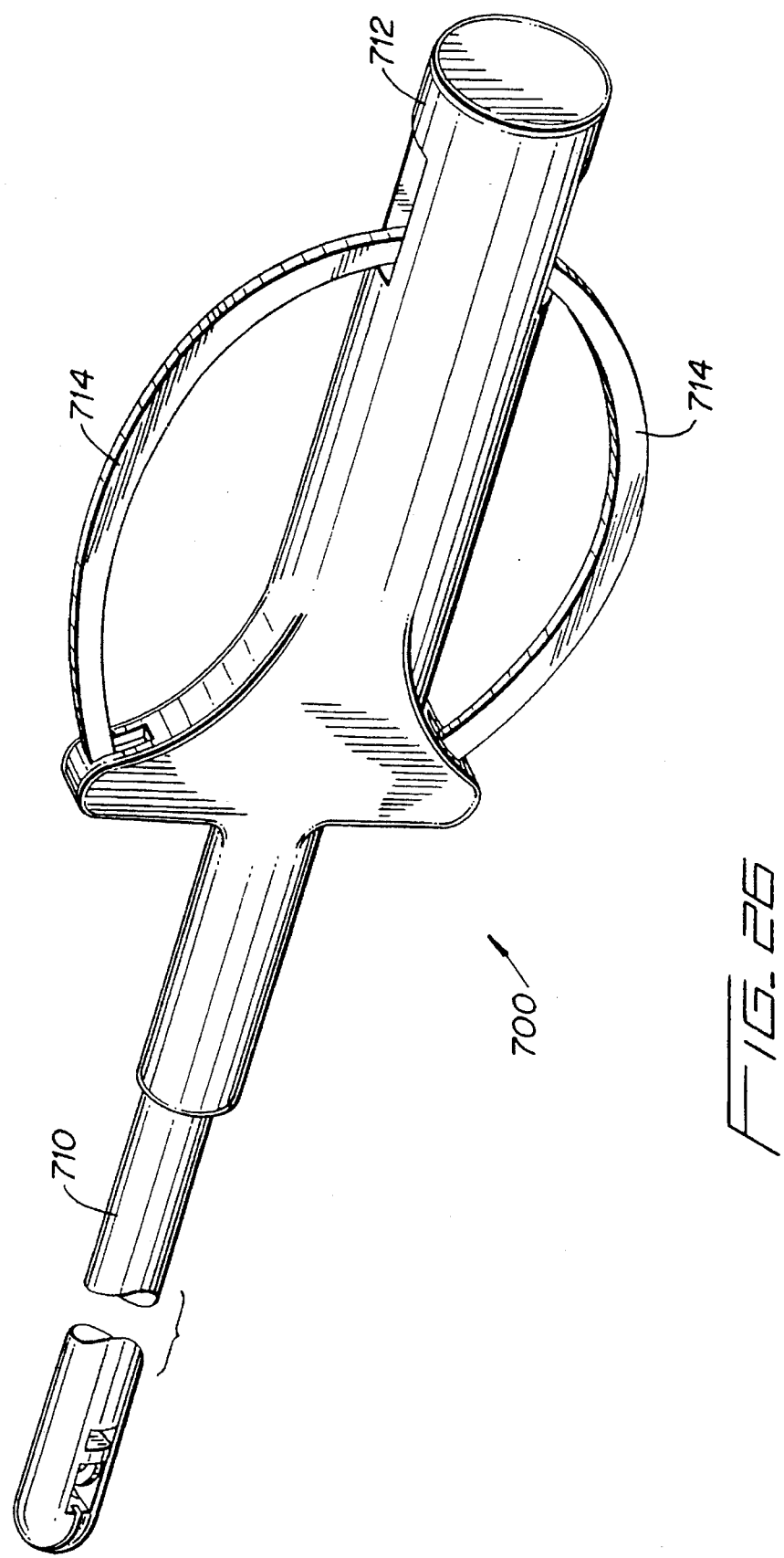

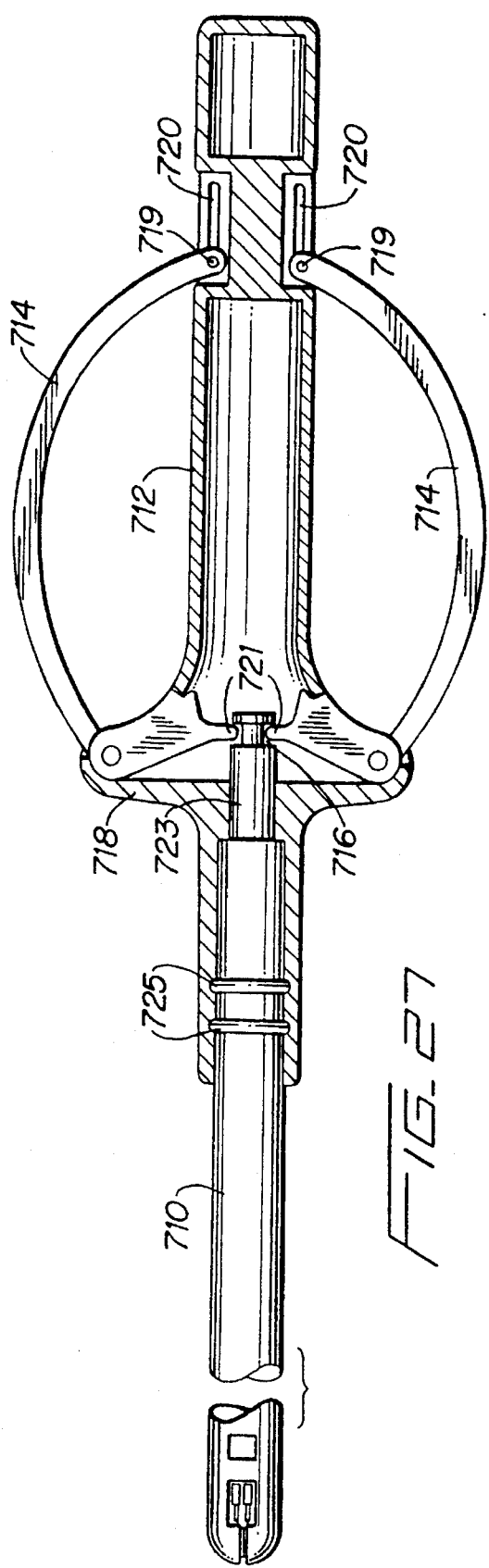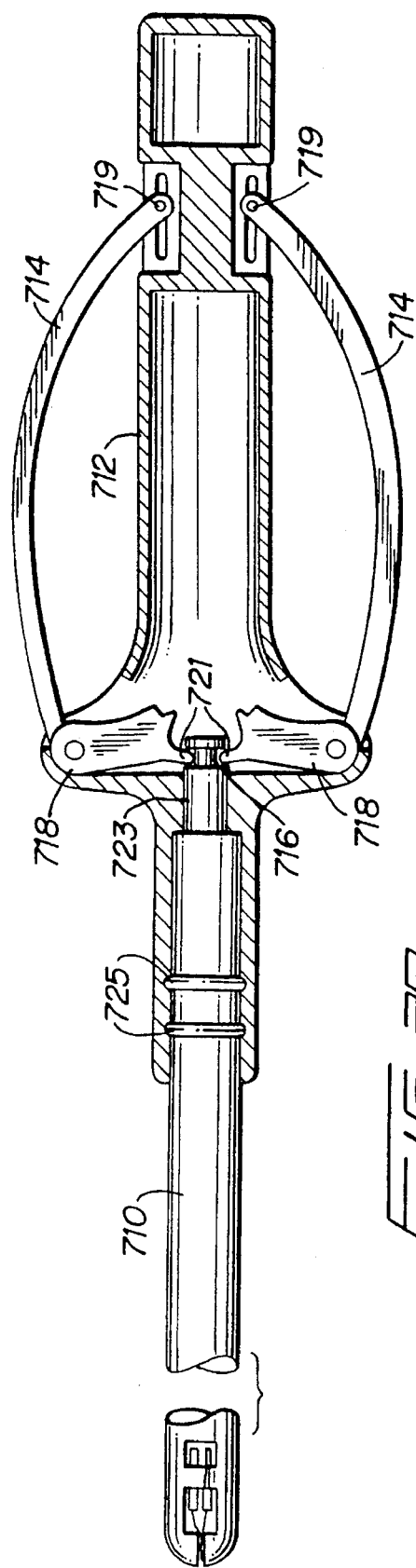

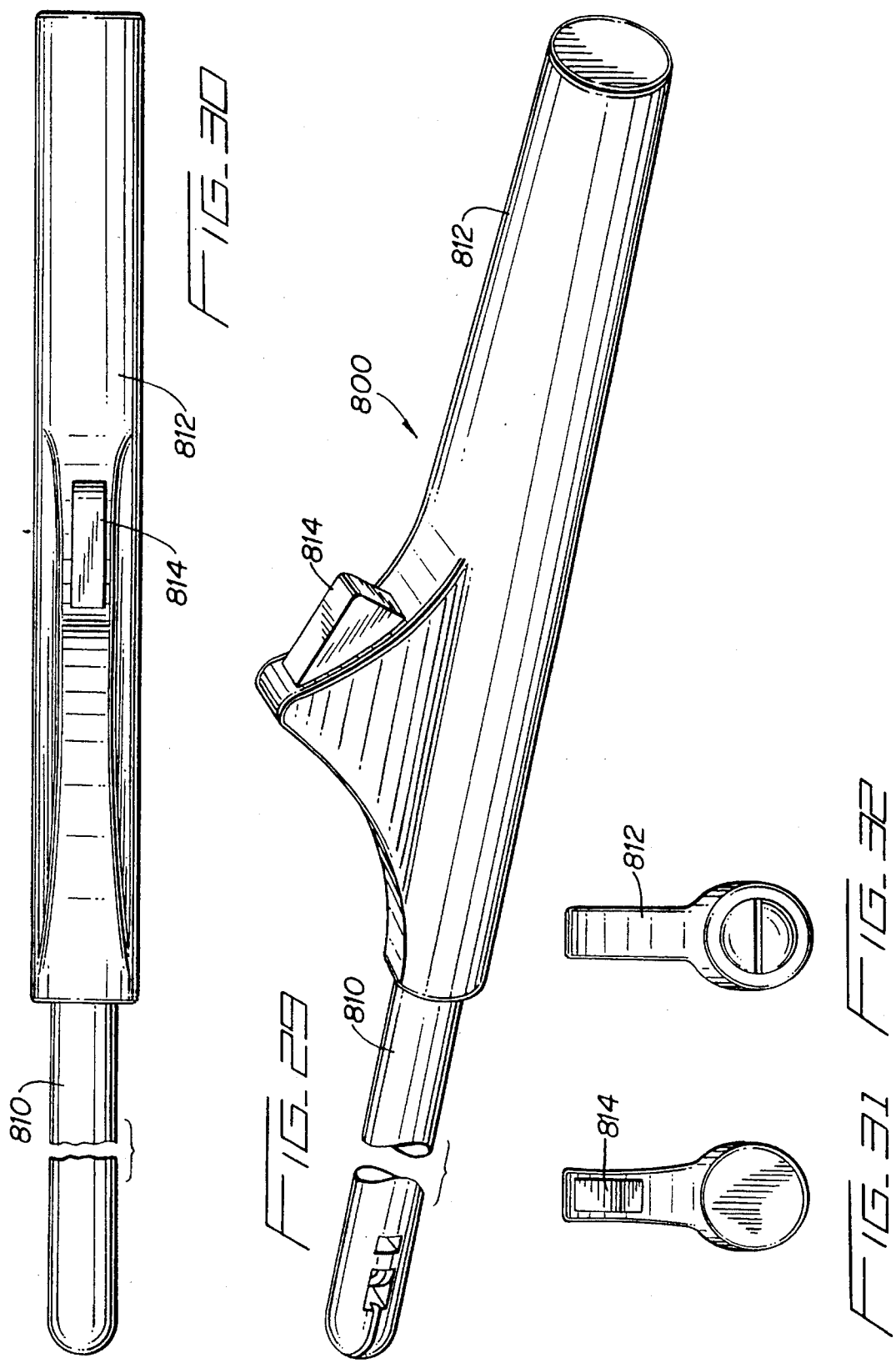

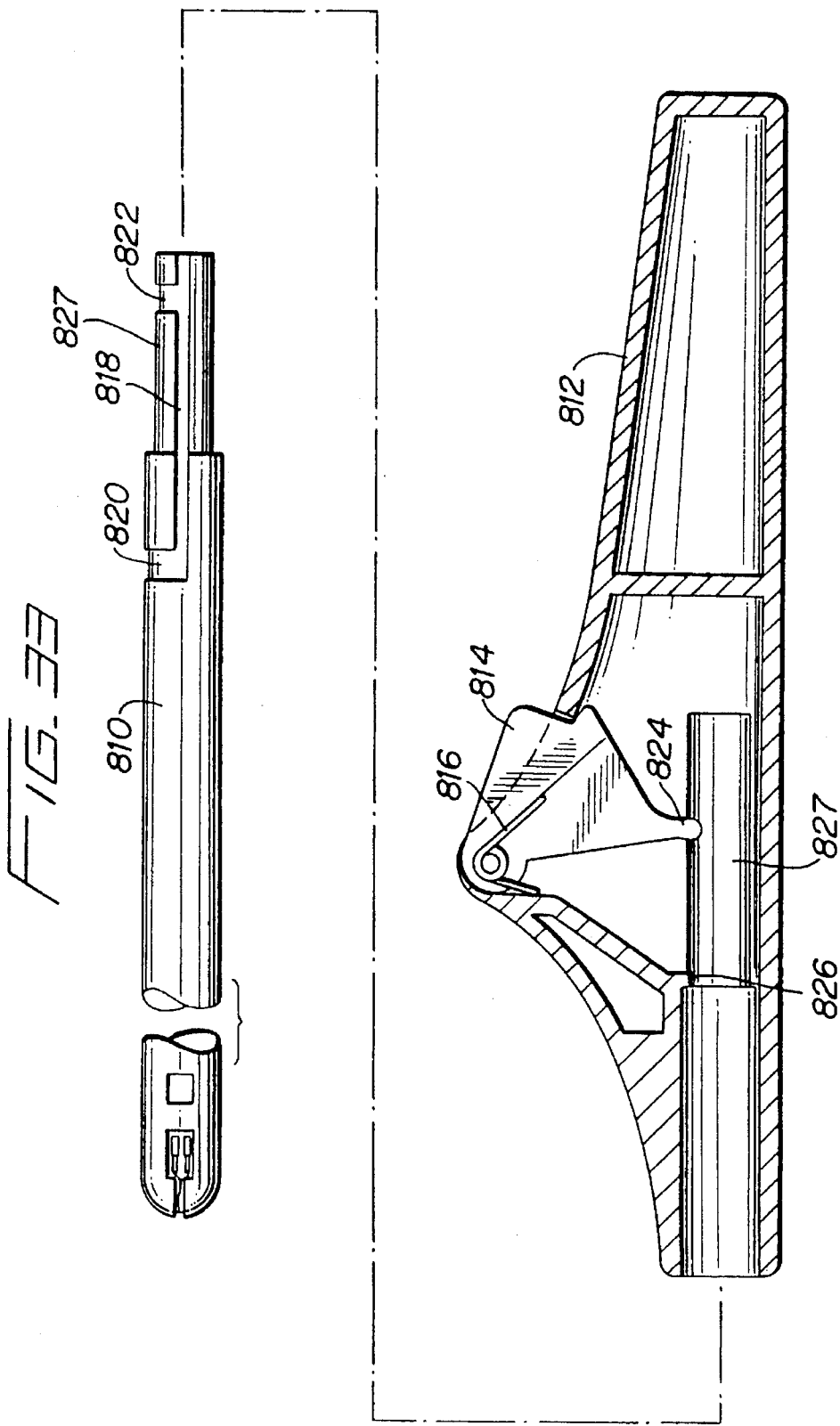

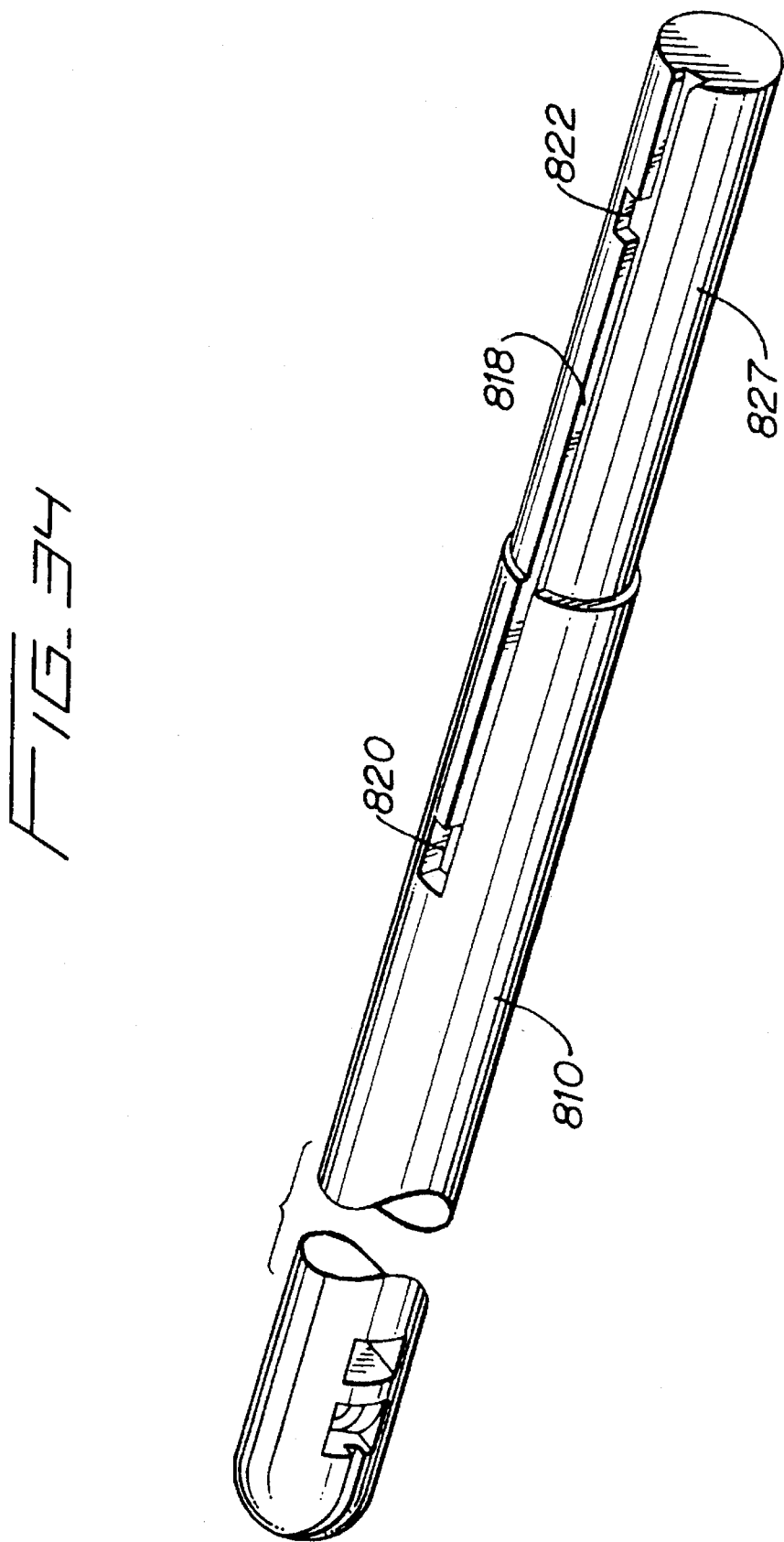

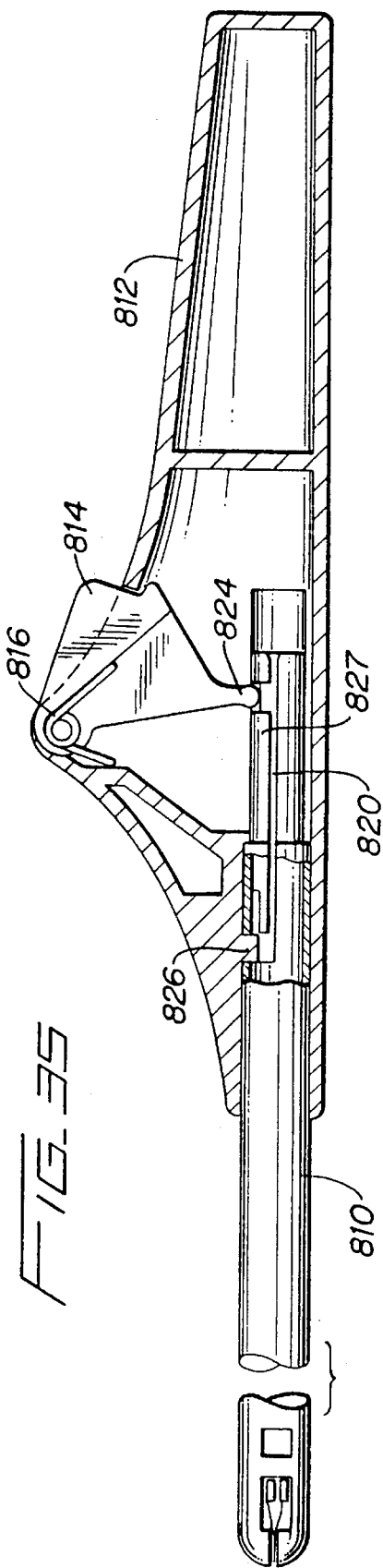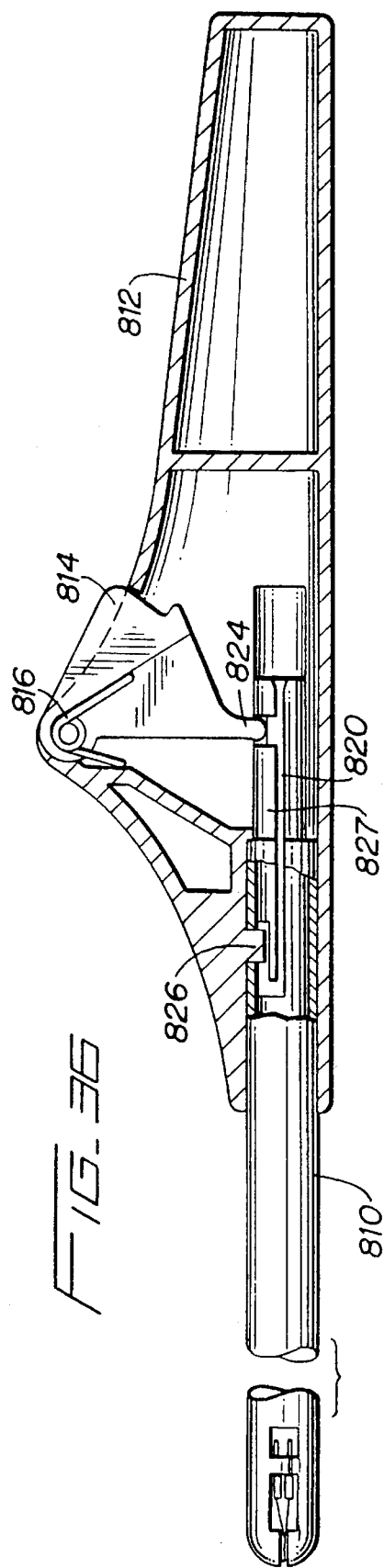

INSTRUMENT FOR CLOSING TROCAR PUNCTURE WOUNDS

BACKGROUND OF THE INVENTION

This is a continuation-in-part application of U.S. Ser. No. 08/134,144 filed on Oct. 8, 1993.

FIELD OF THE INVENTION

This invention relates to instruments for suturing puncture wounds and more particularly to instruments for closing trocar puncture wounds formed during endoscopic surgical procedures.

DESCRIPTION OF THE RELATED ART

With laparoscopic and endoscopic surgery, a small incision or puncture is made in the patient's body to provide access for a tube or a cannula device. Once extended into the patient's body, the cannula allows for insertion of various surgical instruments such as scissors, dissectors, retractors, or biopsy instruments to perform diagnostics and/or surgery. Upon completion of the surgical procedure, the remaining trocar wound may require some attention, e.g., in the form of placing sutures to close the wound. In certain cases it may be desirable to close the wound from within.

A device which forms sutures from within the urethra is shown in Soviet Patent SU 1093329. The device is inserted into the urethra and pivotally deploys needles from which sutures are subsequently pulled through the side walls of the urethra.

Other devices have been developed which are used to place sutures from within a wound. For example, commonly assigned applications Ser. No. 07/950,073 filed Sep. 23, 1992 now abandoned and Ser. No. 08/013,244 filed Feb. 23, 1993 now U.S. Pat. No. 5,403,328 as well as application Ser. No. 07/876,511 now U.S. Pat. No. 5,368,601 relate to different Surgical instruments for placing sutures from within a trocar wound. U.S. patent application Ser. No. 08/091,793, filed Jul. 14, 1993 also discloses a surgical instrument for placing suture, the contents of which are incorporated herein by reference. Also, a device has been developed for placing sutures from within a trocar wound which includes a needle clamping device for capturing the needles upon deployment thereof. Such a device is shown in a product brochure of REMA-Medizintechnik GmbH of Germany.

An improved instrument which provides better deployment and capturing or shielding of the needles is disclosed in commonly assigned co-pending application Ser. No. 08/134,144, filed Oct. 8, 1993, the contents of which are incorporated herein by reference.

It would be advantageous to provide a reloadable instrument which would allow replacement of fresh needles and sutures to close several trocar wounds in the patient.

SUMMARY OF THE INVENTION

The present invention provides a novel surgical instrument for applying sutures through body tissue and includes a lightweight and easy to use instrument which may be operated quickly and efficiently.

In one aspect of the present invention, the instrument includes an elongated body having a proximal end portion and a distal end portion, at least one needle carrier member operatively mounted in the distal end portion and movable between at least a retracted position and a deployed position, a needle releasably retained in the at least one needle carrier member, a predetermined length of suture material having one end affixed to the needle. The instrument may include a suture material tensioning member disposed within the elongated body for maintaining the suture material in tension during movement of the at least one needle carrier member from the retracted position to the deployed position.

The instrument may also include a retaining mechanism adapted to retain the at least one needle carrier in the partially deployed position.

In another aspect of the present invention, the instrument includes an actuator member operatively associated with the at least one needle carrier member, the actuator member being movable between at least a first position and a second position to move the at least one needle carrier from the initial position to the deployed position, a needle retaining member disposed in the elongated body and adapted to retain the needle therein when the at least one needle carrier member is in the deployed position, and a needle skewing mechanism operatively associated with the actuator member such that upon movement of the actuator member from the first position to the second position the needle skewing mechanism contacts a tapered portion of the needle to change the alignment thereof relative to the retaining member.

A deployment indicator may be included in the instrument to provide an indication to an operator of the instrument when the at least one needle carrier member is in the second position.

In alternate embodiments, the instrument is reloadable to provide replacement with fresh needles and sutures to close several trocar wounds in the patient. The elongated housing portion, in one embodiment, is removably mounted to a pistol grip handle housing to intermesh with a gear mechanism for movement between a proximal and distal position to deploy the needle structure. In an alternate embodiment, the instrument comprises a pair of flexible curved members mounted to a grip portion and a pair of levers mounted to the curved members. The elongated member has a groove to receive the levers to provide for distal movement to deploy the needle structure. In another embodiment, the elongated housing is removably mounted by a bayonet mount to the handle portion. The inner rod is deployed by depression of a push button mechanism. These instruments can incorporate the different aspects described above.

BRIEF DESCRIPTION OF THE DRAWINGS

Preferred embodiments of the invention are described herein below with reference to the drawings wherein:

FIG. 1 is a perspective view of one embodiment of the instrument of the present invention;

FIG. 2 is a partial cross-sectional view taken along section line 2—2 of FIG. 1;

FIG. 4 is a cross-sectional view taken along section line 4—4 of FIG. 1;

FIG. 5 is a cross-sectional view taken along line 5—5 of FIG. 4;

FIGS. 6–8 are views similar to FIG. 5, which show the sequential operation of the needle deployment actuating mechanism of the instrument of FIG. 1;

FIG. 12 is a partial plan view of the instrument of the present invention with one half of the elongated body removed to illustrate the suture material tensioning system;

FIG. 13 is a cross-sectional view taken along section line 13—13 of FIG. 12;

FIG. 14 is a view similar to FIG. 12, which shows the suture tensioning system after the deployment of the needles;

FIG. 15 is a cross-sectional view taken along section line 15—15 of FIG. 14;

FIG. 26 is a perspective view of an alternate embodiment of the apparatus of the present invention having a reloadable needle and suture housing and utilizing a pair of flexible handle members for deploying the needle carriers;

FIG. 27 is a partial cross-sectional view of the apparatus of FIG. 26 prior to deployment of the needle carriers;

FIG. 28 is a partial cross-sectional view of the apparatus of FIG. 26 showing the handles squeezed to deploy the needle carriers;

FIG. 29 is a perspective view of another alternate embodiment of the apparatus of the present invention having a reloadable needle and suture housing and utilizing a push button mechanism for deploying the needle carriers;

FIG. 30 is a top view of the apparatus of FIG. 29;

FIGS. 31 and 32 are rear and front views, respectively, of the apparatus of FIG. 29;

FIG. 33 is an side view of the apparatus of FIG. 29, showing the elongated needle and suture housing separated from the handle portion;

FIG. 34 is a perspective view of the elongated needle and suture housing;

FIG. 35 is a partial cross-sectional view of the apparatus of FIG. 29 prior to deployment of the needle carriers; and FIG. 36 is a partial cross-sectional view showing the button depressed and the needle carriers deployed.

DETAILED DESCRIPTION OF THE PREFERRED EMBODIMENTS

Figure 3:
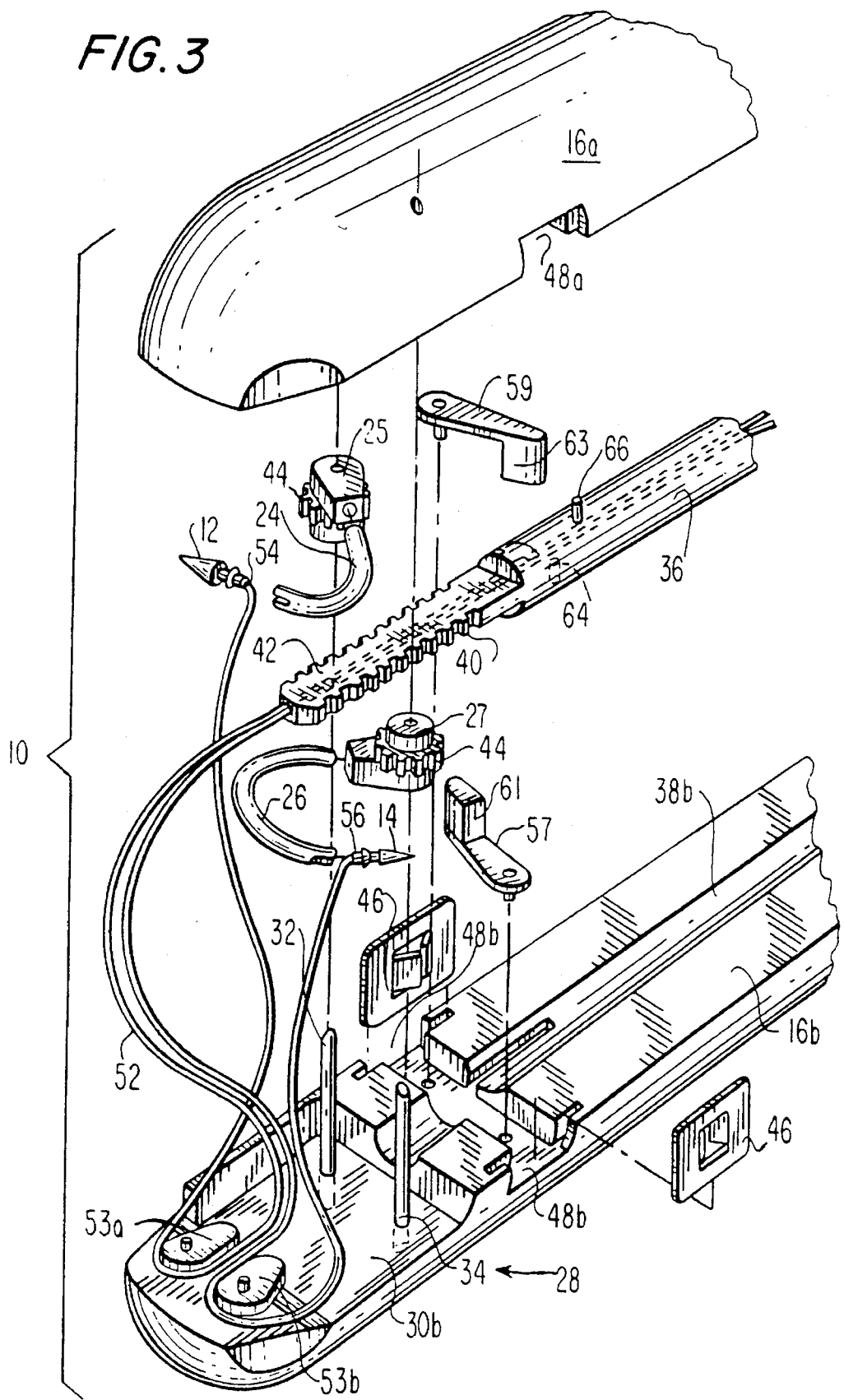
FIG. 3 is an exploded partial-view with parts separated of the distal end of the instrument of FIG. 1.

Referring now in specific detail to the drawings, in which like reference numerals identify similar or identical elements throughout the several views, and initially to FIGS. 1–3, one embodiment of a suturing instrument for closing puncture wounds in accordance with the present invention is shown generally at 10. Suturing instrument 10 is particularly adapted for driving a pair of needles 12 and 14 from within the endoscopic cavity of a patient into the peripheral tissue adjacent an endoscopic puncture wound and placing a suture therein. However, instruments which utilize more or less than two needles are also within the scope of the present invention.

Generally, suturing instrument 10 includes an elongated housing portion, for example, elongated tubular body 16 having actuator button 18 slidably disposed at proximal end 20 and needle deploying means such as needle carrier arms 24 and 26 mounted adjacent distal end 28. Elongated tubular body 16 is suitable for insertion preferably through a trocar cannula or alternately directly into a puncture wound such as a trocar incision wound formed during an endoscopic or laparoscopic surgical procedure. Except where noted otherwise, the materials utilized in the components of the instrument generally include such materials as polycarbonate for housing sections and related components, and stainless steel, particularly for components which transmit forces. One preferred material is a polycarbonate material available from General Electric Company under the trade name LEXAN. Other specific preferred materials such as nylon or glass filled nylon (for strength) may also be utilized. However, equivalent alternative materials will readily come to the mind of those skilled in the art.

In FIG. 3, distal end 28 of instrument 10 is shown with the component parts separated for illustration purposes. Elongated housing portion 16 includes housing half-sections 16a and 16b which are attached by any suitable means, such as for example, fasteners, adhesives, welding, etc. A pair of needles such as needles 12 and 14 are removably mounted such as by slip fitting them to carrier arms 24 and 26, respectively. Carrier arms 24 and 26 are mounted on gear members 25 and 27, respectively, which are operatively mounted on elongated housing portion 16 in cut out portions 30a and 30b formed in housing half sections 16a and 16b, respectively. Gear members 25 and 27 are preferably pivotally mounted on posts 32 and 34 respectively. A boss (not shown) is mounted on post 32 below gear member 25 and another boss (not shown) is mounted on post 34 above gear member 27. These bosses maintain gear members 25, 27 in the same plane.

An actuating member is provided, in the form of elongated rod 36 which is slidably positioned in a bore formed through elongated housing portion 16 and made up of grooves 38a (not shown) and 38b formed in housing half-sections 16a and 16b, respectively. Preferably, grooves 38a and 38b conform in shape to the outer surface of elongated rod 36 so as to facilitate sliding motion of elongated rod 36 within elongated housing portion 16. Elongated rod 36 is provided with teeth 40 formed on both side edges of flattened distal end portion 42. In the illustrated embodiment, distal end portion 42 is shown as being flattened, having a rectangular cross-section. Clearly, any suitable cross-section may be substituted for flattened distal end portion 42 or for rod 36.

Teeth 40 of elongated rod 36 cooperate, i.e. mesh, with teeth 44 of gear members 25 and 27 in a rack and pinion fashion so as to cause carrier arms 24 and 26 to pivot about posts 32 and 34, respectively. Needle retaining means are also provided in the form of latch members 46 which are inserted in slots formed in the walls of housing half sections 16a and 16b on either side of cutout portions 48a and 48b formed in housing half-sections 16a and 16b, respectively. Referring to FIGS. 12 and 13, a suture passageway is provided in elongated rod 36, shown as bore 50 formed along the central longitudinal axis of elongated rod 36 and passing partially therethrough. A suture tensioning member, shown as rolled constant force spring element 51, has tab portion 51a press fit into a cut-out portion 55 of elongated rod 36 so that tab 51a will remain fixed relative to elongated rod 36 upon actuation of instrument 10. Referring once again to FIG. 3, a suitable suture material such as suture 52 is thereby stored and fed through bore 50 (FIG. 15) and passes around suture guides 53a and 53b (FIG. 3) mounted between housing half-sections 16a and 16b, respectively, and spaced from the end of instrument 10 so that suture material 52 is not exposed at the bottom of the instrument. Suture 52 is attached to proximal ends 54 and 56 of needles 12 and 14, respectively.

Also mounted on elongated body 16 are needle kinking members such as arms 57 and 59 which are preferably pivotably mounted to housing half-section 16b. Clearly arms 57 and 59 could also be mounted one on each housing half section 16a and 16b or both on housing half-section 16a. Arms 57 and 59 have needle contacting surfaces extending therefrom such as extended portions 61 and 63, respectively. Camming pins 64 and 66 are preferably press fit into bores formed on opposite sides of elongated rod 36, as shown in FIG. 3. The operation of arms 57 and 59 in cooperation with camming pins 64 and 66 will be explained in detail further herein below.

Figure 9:
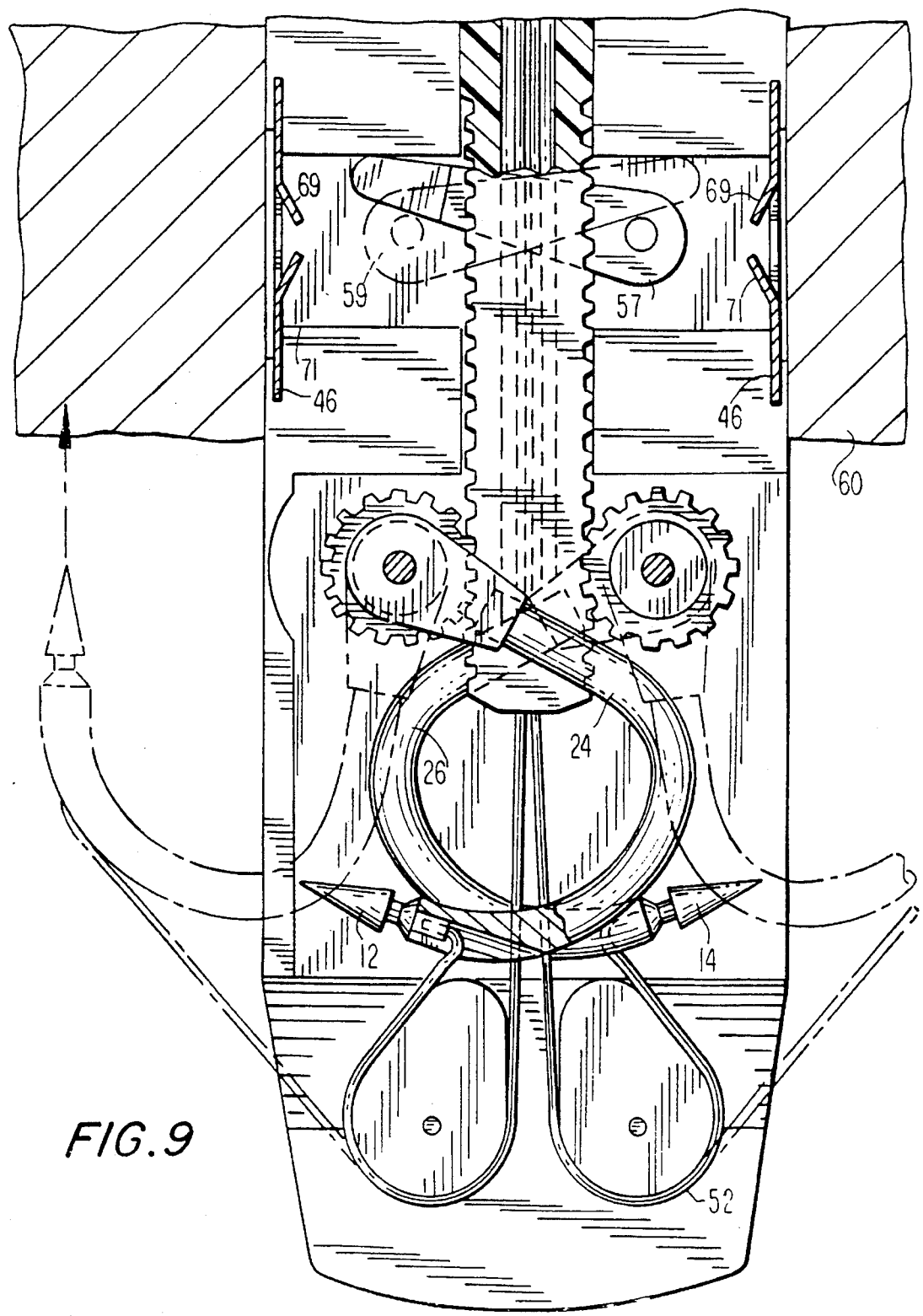
FIG. 9 is a cross-sectional view of the distal end of the instrument taken along section line 9—9 of FIG. 1 and showing the needle carriers in the intermediate position in phantom lines.

As shown in FIG. 2, elongated rod 36 is spring biased in a proximal direction corresponding to a retracted position of needles 12 and 14, illustrated in FIGS. 1 and 9. In the retracted position, needles 12 and 14 are preferably disposed completely within elongated housing portion 16. This facilitates insertion and removal of suturing instrument 10 without undesired contact of needle 12 and 14 with either the patient's tissue or that of the operating room personnel.

Referring now to FIGS. 4–8, the mechanism for retaining needle carriers 24 and 26 in the partially deployed position as shown in phantom lines in FIG. 9, will now be described. FIGS. 4 and 5 illustrate the various structural components of the retaining mechanism. Pivot arm 68 is pivotally mounted on housing half-section 16a and is spring biased to align parallel with a longitudinal axis of housing half-section 16a. Latch member 70 is securely mounted to the proximal end of pivot arm 68 or alternatively can be integral therewith. Post member 72 is mounted on elongated rod 36, preferably in line with the central longitudinal axis of pivot arm 68, so that post member 72 is situated immediately proximal to the proximal end of pivot arm 68 when the instrument is in the fully retracted position.

In operation, suturing instrument 10 is inserted, in its initial or fully retracted position, as shown in FIG. 9, in a puncture wound such as the type created by a trocar during endoscopic or laparoscopic surgical procedures. Preferably the instrument is inserted into the incision wound (in the direction of arrow A in FIG. 9) so that proximal end 58 of the opening formed by cutouts 30a and 30b is situated immediately below the fascia, designated as 60 in FIG. 9. Separate indicating means (not shown) may be provided on suturing instrument 10 to apprise the user as to when suturing instrument 10 is in the preferred position.

Alternatively, suturing instrument 10 may be inserted through an appropriately sized trocar situated in a body wall. Once suturing instrument 10 is adequately inserted, the trocar may be removed leaving suturing instrument 10 in place.

With suturing instrument 10 situated in the appropriate position, actuating button 18 (FIG. 1) is depressed thereby urging elongated rod 36 in a distal direction causing teeth 40 to rotate carrier arms 24 and 26, due to the meshing of teeth 40 with teeth 44 of the gear members 25 and 27. As actuator button 18 is depressed, post member 72, which as noted above is mounted to elongated rod 36, moves distally, as shown in FIG. 6. Post member 72 contacts leading edge 74 of latch member 70 and the camming action resulting from the sliding contact between the continued distal motion of post member 72 and leading edge 74 causes pivot arm to rotate counter-clockwise in the direction of Arrow A of FIG. 6. With continued distal motion of elongated rod 36, post member 72 passes becomes latched, as shown in FIG. 7. This position corresponds with the intermediate position of needle carrier arms 24 and 26 as shown in phantom lines in FIG. 9.

The initial rotation of needle carrier arms to their intermediate position causes suture material 52 to pull in a distal direction consequently causing rolled spring element 51 (FIGS. 12 and 13) to unravel slightly while maintaining tension in suture material 52.

With the carrier arms disposed in the intermediate position, the user can then pull the instrument proximally toward the surface of the trocar incision and embed the needles in the fascia. Once the needles have been embedded in fascia 60, the instrument is then preferably fully deployed by depressing actuator button 18 to its distal-most position. Needles 12 and 14 are thereby rotated on carrier arms 24 and 26 such that needles 12 and 14 continue through fascia 60 allowing the needles to pass through a portion of the fascia and surrounding tissue. (See arrow B in FIG. 10). The complete depression of actuator button 18 causes post member 72 to move distally to disengage with latch member 74 enough so that the spring biased pivot arm 68 returns to its centrally aligned orientation, which causes latch member 74 to drop below post member 72, as shown in FIG. 8. Thus, when the appropriate time occurs, the release of actuator button and the resulting proximal movement of the spring biased elongated rod 36 will cause post member 72 to cam trailing edge 76 of latch member 70 such that post member 70 passes around latch member 70 and returns to its proximal-most position.

Figure 10:
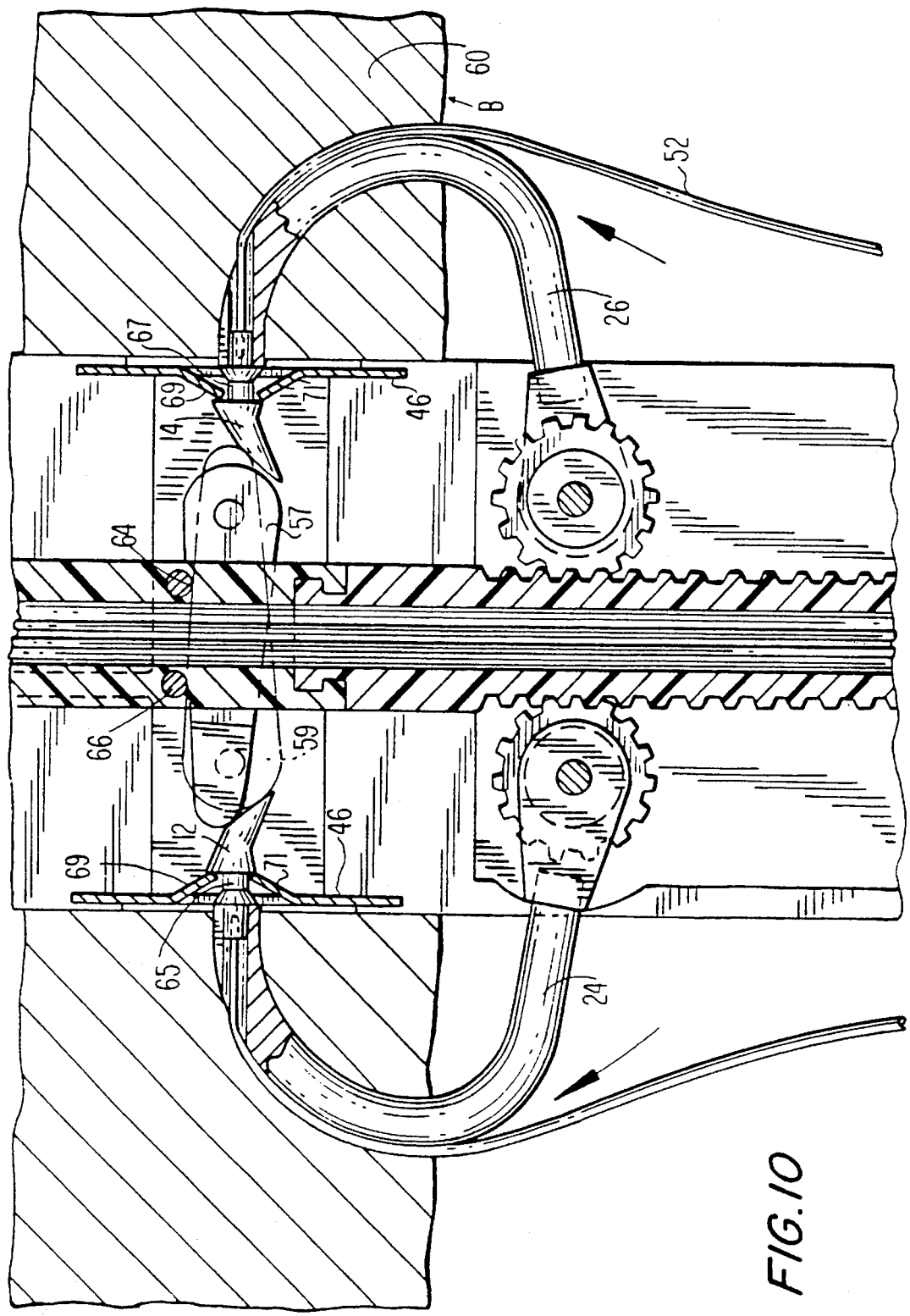
FIG. 10 is an enlarged view of the needle deployment mechanism showing the needle carriers in the fully deployed position.

Upon complete depression of actuator button 18, needles 12 and 14 become latched in latch members 46. One way of achieving the latching is shown as the pointed end passes through the gap between flap portions 65 and 67 and cam flap portions open until they seat in annular groove portions 65 and 67 of needles 12 and 14, as best shown in FIG. 10. To insure that needles 12 and 14 are retained in latch members 46, a needle kinking mechanism is preferably incorporated in the instrument and constructed to automatically strike the pointed ends of the needles as soon as they are completely within latch members 46. When actuator button 18 is completely depressed, camming pins 66 and 64, which are mounted on elongated rod 36, contact pivot arms 57 and 59 causing them to pivot distally and thus strike the pointed ends of needles 12 and 14, thereby deforming them, as shown in FIG. 10.

The complete depression of actuator button 18 and the corresponding distal movement of elongated rod 36 and fully deployed position of needle carrier arms 24 and 26 causes suture material 52 to pull rolled spring element 51 (FIGS. 14 and 15) to completely unravel and release suture material 52 therefrom. In FIG. 15 rolled spring element is shown an instant before needle carrier arms reach their fully deployed position. At true full deployment of needle carrier arms 24 and 26, end 51b of rolled spring element releases suture material 52 so that it may be passed through the path created in fascia 60 by needles 12 and 14.

Figure 11:
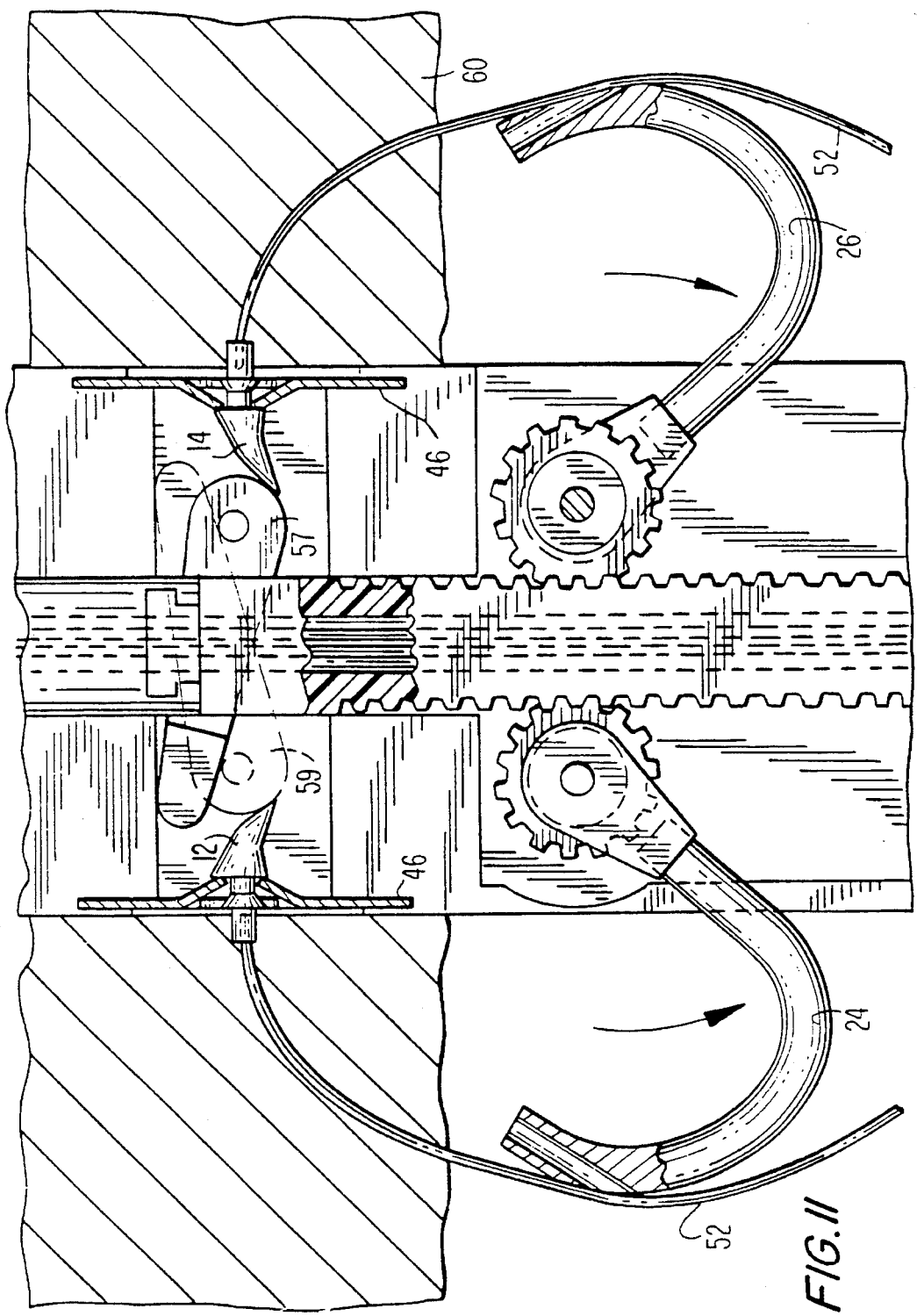
FIG. 11 is an enlarged view similar to FIG. 10, which shows the needle carriers retracting after the needles have become embedded in the needle retaining members.

Actuator button 18 is released allowing elongated rod 36 to return to its proximal or initial position and needle carrier arms 24 and 26 to return to their retracted positions within elongated housing portion 16 leaving needles 12 and 14 attached to latch members 46, as shown in FIG. 11. Suturing instrument 10 is pulled out of the trocar incision causing suture 52 (still attached to needles 12 and 14 which are latched onto suturing instrument 10) to be pulled through fascia 60 following the path taken by needles 12 and 14 and up through the remainder of the trocar incision until exiting the opening at the surface of the skin. Suture 52 is grasped and preferably cut away from needles 12 and 14 and thereafter tied off in the appropriate surgeon's knot.

Figure 17:
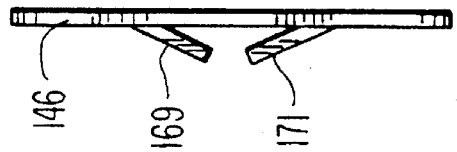
FIGS. 16–19 illustrate two alternative needle retaining members for use with the instrument of the present invention.
Figure 19:
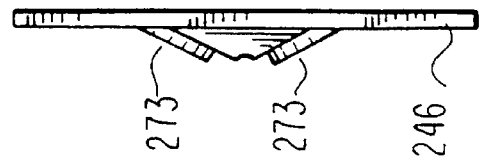
Figure 16:
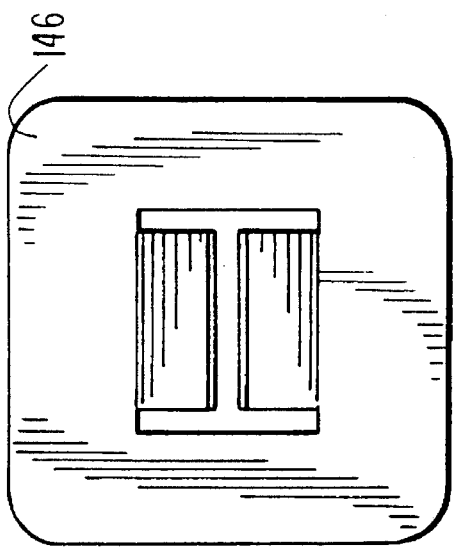
Figure 18:
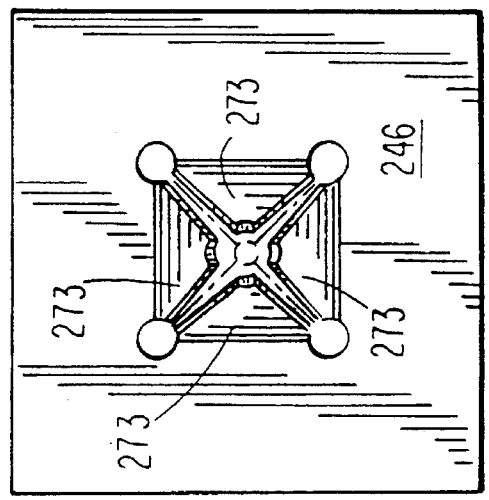

FIGS. 16–19 illustrate alternative embodiments of the needle latch member of the present invention. In FIGS. 16 and 17 latch member 146 is shown having flap portions 169 and 171 which are oriented at 90 degrees relative to flap members 69 and 71 of latch member 46. FIGS. 18 and 19 illustrate latch member 246 having four flap portions 273 orthogonally situated so as to receive the pointed end of needles 12 and 14 through the central region thereof.

Figure 20:
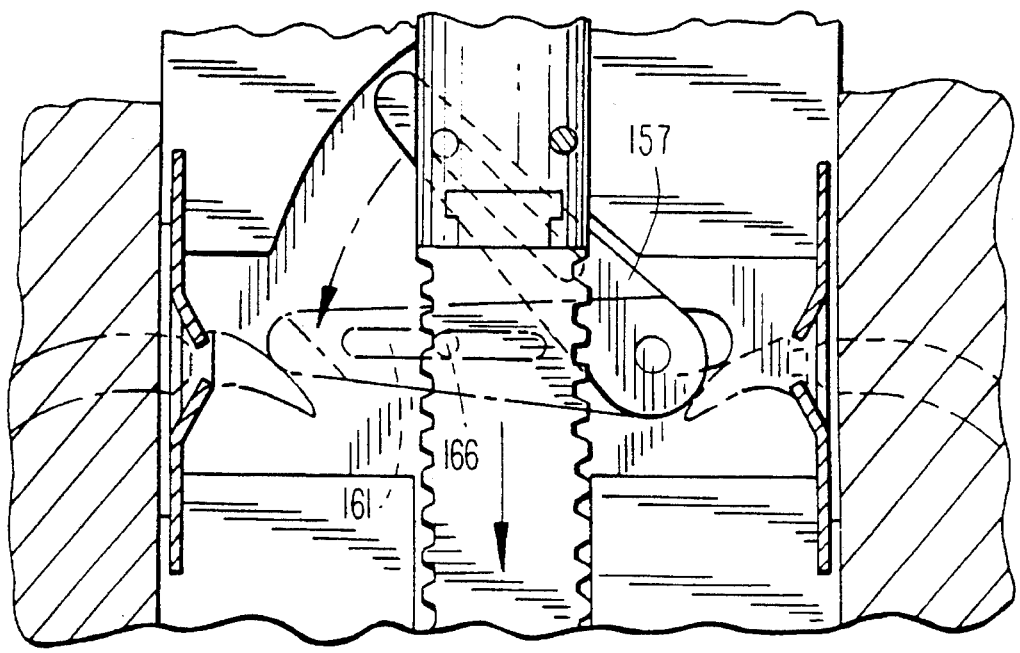
FIG. 20 is another embodiment of the needle skewing mechanism for use with the instrument of the present invention.

FIG. 20 illustrates an alternative embodiment of the arm component of the needle skewing mechanism of the present invention. Arm 157 is shown having camming slot 161 formed thereon so that camming pin 166 is in constant sliding contact with arm 157 as compared with the momentary sliding contact camming pins 64 and 66 have with arms 57 and 59.

Figure 21:
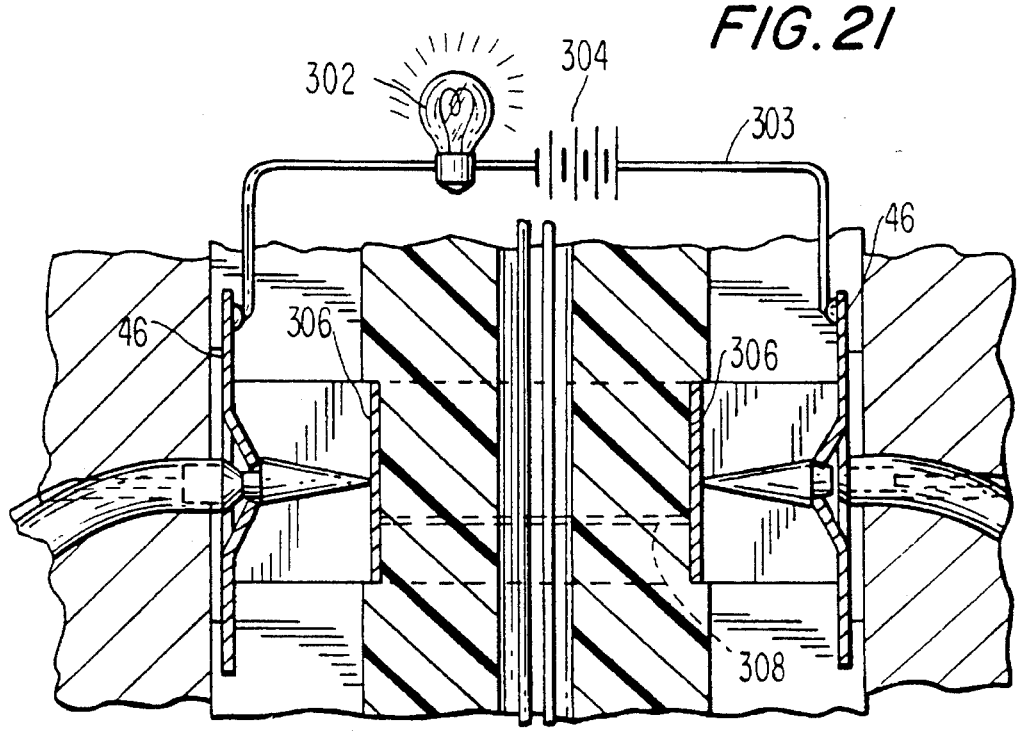
FIG. 21 illustrates the deployment indicator for the instrument of the present invention.
Figure 22:
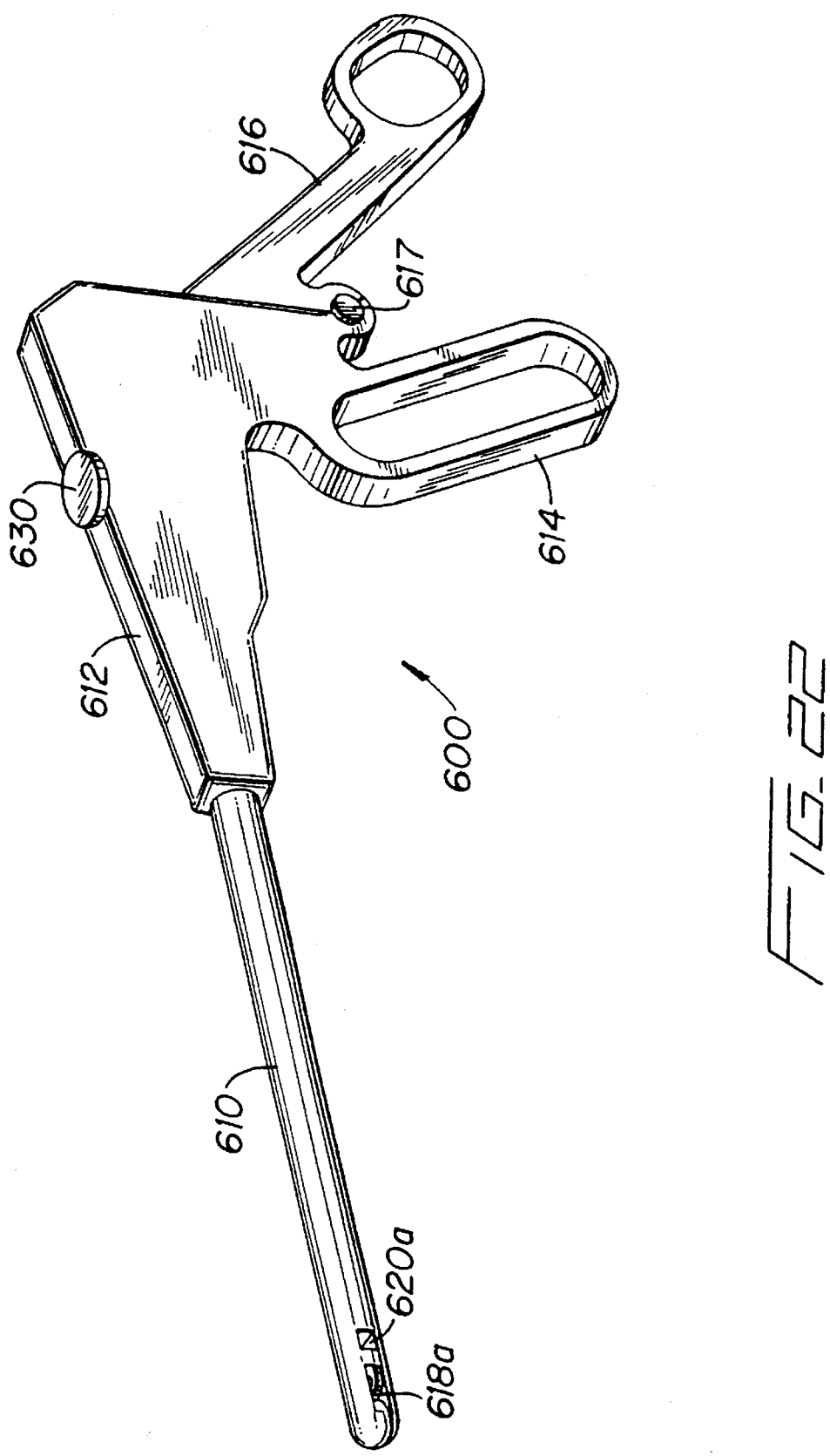
FIG. 22 is a perspective view of a first embodiment of the apparatus of the present invention having a reloadable needle and suture housing and utilizing a pistol grip for deploying the needle carriers.
Figure 23:
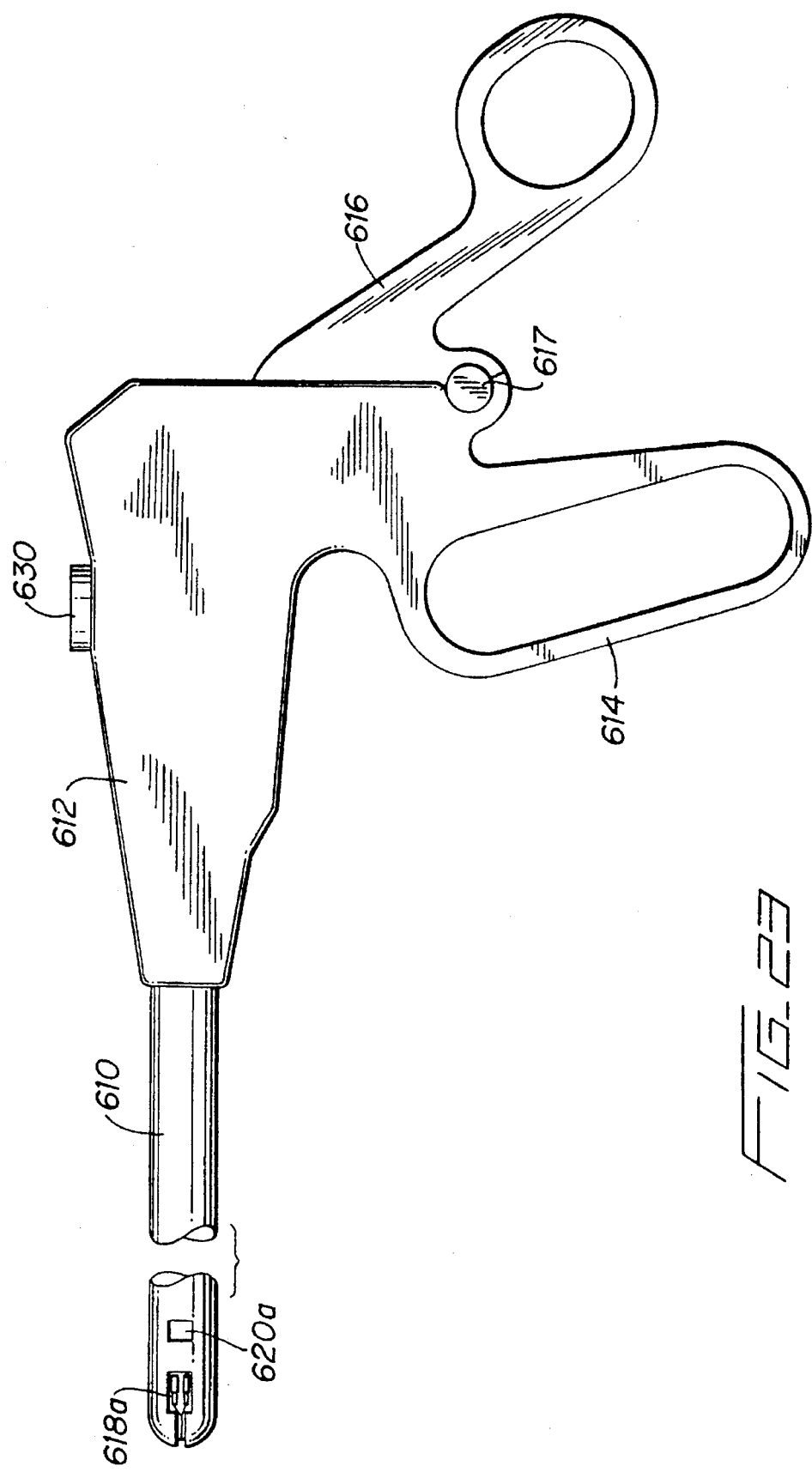
FIG. 23 is a side view of the apparatus of FIG. 22.
Figure 24:
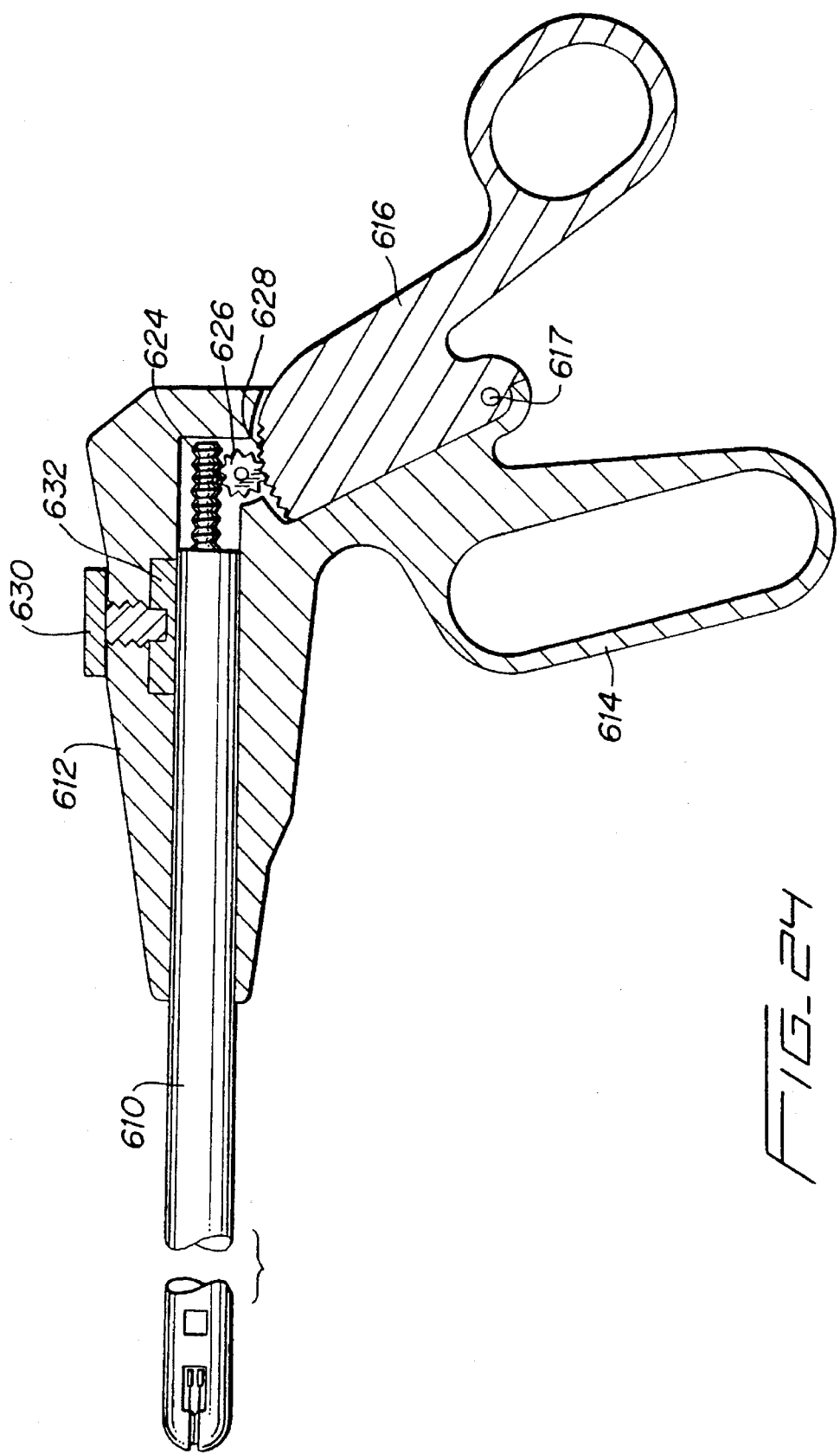
FIG. 24 is a partial cross-sectional view of the apparatus of FIG. 22 prior to deployment of the needle carriers.
Figure 25:
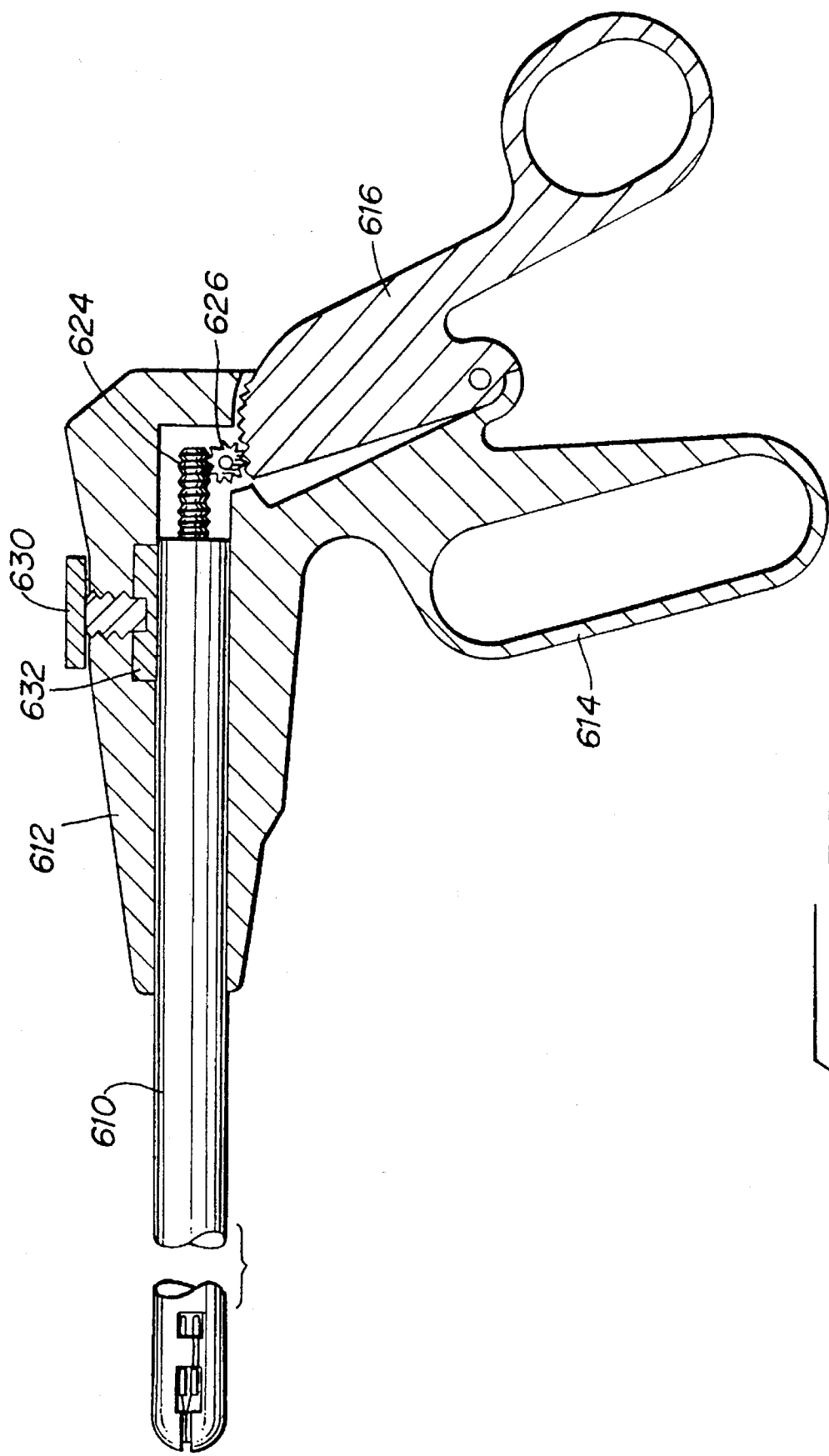
FIG. 25 is a partial cross-sectional view of the apparatus of FIG. 22 showing the handle squeezed to deploy the needle carriers.

In FIG. 21 a needle deployment indicator is illustrated schematically with indicator light 302 being connected in a simple series circuit by wire 303 with a power source, such as battery 304 and latch members 46. The circuit is complete when the pointed ends of needles 12 and 14, which are electrically conductive, contact the electrically conductive plates 306 which are in turn connected by bridge wire 308.

The indicator light 302 is preferably positioned adjacent a proximal portion of the instrument to visually indicate to the user that the needles are securely embedded in latch members 46. Thus the connecting wires 303 would extend the length of the elongated body 16. Alternately, the indicator can be positioned adjacent a distal end of the elongated body 16, and if a visual indicator is provided, it can be viewed on the TV monitor used in the laparoscopic procedure.

The indicator is preferably an LED, however other devices which emit a detectable response to an electrical current can also be utilized, such as incandescent lamps, liquid crystal displays (LCD's), audible indicators, tactile indicators and light/temperature responsive materials.

FIGS. 22–36 illustrate three different embodiments wherein the elongated housing portion is removably mounted to the handle portion of the instrument to enable reloading the instrument with fresh needles and suture. Consequently the instrument can be used to close several trocar puncture wounds in the patient.

Turning to the first embodiment of the reloadable instrument, and more particularly to FIGS. 22–25, instrument 600 includes elongated housing portion or tubular body 610 and handle assembly 612 having a stationary grip portion 614 and a movable handle 616 pivotally mounted thereto by pivot pin 617.

The distal end portion of elongated housing portion 610 is similar to the elongated tubular body 16 of FIGS. 1–3 in that it includes a pair of needles mounted on carrier arms and an inner elongated rod cooperating with the gear members mounted on the carrier arms. Cut-out portions 618A and 620A are identical to cut-out portions 30B and 48B of FIG. 2, respectively, and the actuation of the carrier arms, i.e. deployment and subsequent latching of the needles within the housing, occurs in an identical manner. Therefore, these features will not be discussed in detail again. However, the mechanism for actuating the inner elongated rod in FIGS. 22–25 differs from that of FIGS. 1–3. The proximal end portion of the inner elongated rod terminates in a plurality of teeth 624. These teeth 624 cooperate with gear 626 which is interposed between teeth 624 and teeth 628 on handle 616. Thus, movement of handle 616 towards handle 614 rotates gear 626 counterclockwise which moves the elongated inner rod from its proximal position of FIG. 24 to its distal position shown in FIG. 25. This deploys the carrier arms and moves the needles into engagement with the latch member as described in detail above with respect to FIGS. 1–3.

When the handle 616 is released, the inner elongated rod returns to its proximal position (FIG. 24) and carrier arms return to their retracted positions within the elongated housing portion 610, leaving the needles latched in the latch member (see e.g. FIG. 11). The suturing instrument is pulled out of the trocar incision, causing the suture to be pulled through the fascia, and the suture is grasped and preferably cut away from the needles and tied off as described above. If the user desires to close another trocar wound with the instrument, screw 630 is rotated to release the pressure, i.e. frictional engagement, of retainer member 632 on elongated housing portion 610. This allows the elongated housing portion 610 to be pulled distally and removed from the handle portion of the instrument. A fresh tubular body 610, having a fresh pair of needles and a suture, (as well as carrier arms, gear mechanism and the other components as described above) can then be inserted into the handle portion 612 and secured therein by tightening of screw 630 to force retaining member 632 to clamp down on tubular body 610. The instrument is then ready to be used again, i.e. inserted into the body to close another trocar puncture wound.

FIGS. 26–28 illustrate an alternate embodiment of the instrument of the present invention having a removable/replaceable elongated housing portion. The instrument 700 includes a tubular handle housing portion 712, a pair of flexible curved handle members 714 and an outer tubular body 710. The tubular body 710 is identical to the elongated tubular body 610 of FIGS. 22–26, except an elongated inner rod 723 has a proximally positioned circumferential recess 716 (instead of teeth) dimensioned to receive lever arms 718. A pair of compression rings 725 are provided within housing portion 712 to help retain the tubular body 710.

In use, squeezing handles 714 towards tubular handle housing portion 712, causes pins 719 to slide proximally in slots 720 and lever arms 718 to pivot clockwise. The engagement of the fingers 721 of lever arms 718 in recess 716 forces the inner elongated rod 723 distally (FIG. 28) to deploy the carrier arms and needles as described above. After use, the handles 714 are released, thereby springing back to their original position (FIG. 27) and returning the elongated inner rod 723 to its initial position. To remove outer tubular body 710, it is rotated so upper and lower slots (not shown) formed in inner rod 723 are aligned with the finger 721 of each lever arm 18, and then pulled distally away from handle housing portion 712. A fresh tubular body with fresh needles and suture can then be inserted.

FIGS. 29–36 illustrate an alternate handle design for actuating the inner rod. Instrument 800 includes elongated tubular handle housing 812, outer tubular body 810, and push button 814 for actuating the elongated inner rod 827. Except for the slot arrangement 818 described below, the outer tubular body 810 and the components contained therein are identical to that described in reference to FIGS. 22–26. Slot arrangement 818, which provides a bayonet type mount, includes a distal recess 820 and a proximal recess 822. Push button 814 is biased outwardly through handle housing 812 by spring 816. Projection 824 of push button 814 is adapted to cooperate with proximal recess 822. Projection 826 of tubular housing 812 cooperates with distal recess 820 to prevent distal movement of outer tubular body 810.

In operation, when push button 814 is pressed inwardly, from the position of FIG. 35 to the position of FIG. 36, projection 824 forces the elongated inner rod 827 distally to actuate the needle carriers and needles as described in detail above. After use, button 814 is released allowing inner elongated rod 827 to return to its initial proximal position of FIG. 35. To remove outer tubular body 810 to allow replacement with a fresh needle and suture arrangement, tubular body 18 is rotated so that projection 824 of button 814 and projection 826 of tubular housing 812 are in alignment with elongated slot 818. Tubular body 810 can then be removed and a new tubular body initially inserted so that elongated slot 818 aligns with projections 824, 826 and then rotated so the projections 824, 826 are positioned within recesses 822, 820 respectively.

It should be understood that the embodiments of FIGS. 22–36 may optionally include a suture tension member, a retaining mechanism to retain the needle carrier in the partially deployed position, a needle skewing mechanism and/or an indicator to inform the user that the needles are securely latched.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above but not limited thereto, are to be considered within the scope of the invention.

What is claimed:

1. A surgical instrument for applying sutures through body tissue, which comprises
    (a) a handle assembly;
    (b) an elongated housing extending from said handle assembly and having a proximal end portion and a distal end portion, said elongated housing being removably mounted to said handle assembly;
    (c) at least one needle carrier operatively connected to said elongated housing for carrying at least one needle, said needle carrier being movable between a retracted position and an extended position; and
    (d) at least one needle positioned on said at least one needle carrier, said at least one needle having a sharp tip movable from a protected position to an exposed position to facilitate penetration of tissue.

2. A surgical instrument for applying sutures through body tissue according to claim 1, further comprising an elongated member operatively associated with said handle assembly, said elongated member being slidably disposed within said elongated housing and operable from said proximal end thereof to actuate said at least one needle carrier.

3. A surgical instrument for applying sutures through body tissue according to claim 2, wherein said handle assembly comprises at least one pivotable handle, said pivotable handle cooperating with said elongated member such that movement of said pivotable handle actuates said elongated member.

4. A surgical instrument for applying sutures through body tissue according to claim 3, further comprising a gear associated with said at least one pivotable handle for actuating said elongated member.

5. A surgical instrument for applying sutures through body tissue according to claim 4, wherein said elongated member has a plurality of teeth at a proximal end to cooperate with said gear.

6. A surgical instrument for applying sutures through body tissue according to claim 2, wherein said handle assembly comprises a pair of flexible members cooperating with said elongated member.

7. A surgical instrument for applying sutures through body tissue according to claim 6, wherein said elongated member includes a recess and said handle assembly further comprises a lever operatively associated with each of said flexible members and engagable with said recess to drive said elongated member.

8. A surgical instrument for applying sutures through body tissue according to claim 7, wherein squeezing of said flexible members towards a longitudinal axis of said handle assembly moves said elongated member distally.

9. A surgical instrument for applying sutures through body tissue according to claim 2, wherein said handle assembly comprises an elongated body portion and a button protruding therefrom, said button operatively associated with said elongated member.

10. A surgical instrument for applying sutures through body tissue according to claim 9, wherein said button comprises a pivotable lever having a projecting surface for engaging and driving said elongated inner member distally.

11. A surgical instrument for applying sutures through body tissue according to claim 10, wherein said elongated member has an elongated slot and is mounted to said handle assembly by a bayonet mount arrangement.

12. A surgical instrument for applying sutures through body tissue according to claim 1, wherein said needle carrier includes at least one arm member for holding said at least one needle, said at least one arm member releasably holding said at least one needle.

13. A surgical instrument for applying sutures through body tissue according to claim 1, further comprising means associated with said elongated housing for receiving and retaining said at least one needle.

14. A surgical instrument for applying sutures through body tissue according to claim 1, further comprising means for releasably securing said elongated housing within a longitudinal bore of said handle assembly.

15. A surgical instrument for applying sutures through body tissue according to claim 14, wherein said releasably securing means comprises a rotatable screw.

16. A surgical instrument for applying sutures through body tissue according to claim 1, further comprising an actuator movably positioned in said elongated housing, wherein the at least one needle carrier is deployable by movement of the actuator.

17. A surgical instrument for applying sutures through body tissue comprising:
   (a) handle assembly having a grip portion and at least one pivotable member;
   (b) an elongated housing removably mounted to said handle assembly and having a proximal end and a distal end;
   (c) at least one needle;
   (d) means operatively connected to said elongated housing, for carrying and deploying said at least one needle having a sharp tip, said carrying and deploying means including at least one needle carrier associated with said distal end of said elongated housing for carrying at least one needle, said at least one needle carrier being movable between a retracted position such that said sharp tip of said at least one needle is disposed substantially within said elongated housing and an extended position upon movement of said pivotable member relative to said grip portion.

18. A surgical instrument for applying sutures through body tissue according to claim 17, further comprising means positioned within said elongated housing for receiving and retaining said at least one needle.

19. A surgical instrument for applying sutures through body tissue according to claim 18, wherein said handle assembly is configured as a pistol grip.

20. A surgical instrument for applying sutures through body tissue according to claim 16, wherein said pivotable member is spring biased to first position so that said needle carrier is biased to said retracted position.

21. A surgical instrument for applying sutures through body tissue comprising:
   (a) a handle assembly having a grip portion, at least two pivotable members and a pair of flexible members operatively associated with said at least two pivotable members;
   (b) an elongated housing extending from said handle assembly and having a proximal end and a distal end;
   (d) at least one needle carrier associated with said distal end of said elongated housing, said at least one needle carrier configured and dimensioned to carry said at least one needle and being movable between a retracted position and an extended position upon movement of said at least two pivotable members.

* * * * *